(12) United States Patent
Frantz et al.

(10) Patent No.: US 7,578,995 B2
(45) Date of Patent: Aug. 25, 2009

(54) PEARLIZER CONCENTRATE AND ITS USE IN PERSONAL CARE COMPOSITIONS

(75) Inventors: Seren Frantz, Phoenix, AZ (US); Stewart Alexander Warburton, West Windsor, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 12/229,028

(22) Filed: Aug. 19, 2008

(65) Prior Publication Data

US 2008/0319090 A1 Dec. 25, 2008

Related U.S. Application Data

(62) Division of application No. 10/758,403, filed on Jan. 15, 2004, now abandoned.

(51) Int. Cl.
*A61Q 5/02* (2006.01)
(52) U.S. Cl. ............... 424/70.19; 424/70.22; 424/70.27
(58) Field of Classification Search ................... None
See application file for complete search history.

(56) References Cited

U.S. PATENT DOCUMENTS 4,486,334 A * 12/1984 Horiuchi et al. ............... 516/77

* cited by examiner

*Primary Examiner*—Jyothsna A Venkat

(57) ABSTRACT

An aqueous pearlescent concentrate, containing a pearlizing agent, an anionic surfactant, and a cationic component, having increased opacity and is useful in modifying the appearance of aqueous liquid compositions, particularly personal care compositions.

3 Claims, No Drawings

PEARLIZER CONCENTRATE AND ITS USE IN PERSONAL CARE COMPOSITIONS

CROSS-REFERENCE TO RELATED APPLICATION

This application is a divisional application of U.S. application Ser. No. 10/758,403, filed Jan. 15, 2004

FIELD OF THE INVENTION

This invention relates to pearlizer concentrates, more particularly to pearlizer concentrates for use in personal care compositions.

BACKGROUND OF THE INVENTION

Pearlescent additives are commonly used to modify the appearance of personal care compositions. The appearance modification imparted by such additives is influenced by the opacity and shine exhibited by the relevant additive and may range from a highly pearlescence appearance, that is, an iridescent opacity, wherein the pearlizing additive exhibits a high shine, to no pearlescence, that is, a dull or matte opacity, wherein the pearlescent additive exhibits no shine.

Pearlescent additives are typically crystalline materials. The appearance imparted by a pearlescent additive is believed to arise from the crystal morphology of the pearlescent additive. While pearlescent characteristics may be generated in-situ, i.e., by directly adding a pearlescent additive during blending of the product formulation, it is common to add pearlescent additives in the form of a pearlizing concentrate. Use of a pearlizing concentrate allows increased consistency and allows for a reduction in the manufacturing time required for making the finished formulation.

Since the appearance imparted by pearlescent additives is influenced by the opacity and shine characteristics of such additives, it would be beneficial if the opacity and shine characteristics of such additives could be controlled.

SUMMARY OF THE INVENTION

In a first aspect, the present invention is directed to an aqueous pearlescent concentrate, comprising:
a pearlizing agent,
an anionic surfactant, and
a cationic component.

The pearlizing concentrate of the present invention provides increased opacity and in some embodiments, increased shine.

In a second aspect, the present invention is directed to a method for making an aqueous pearlescent composition, comprising providing a heated aqueous mixture comprising a molten pearlizing agent, cooling the mixture to allow formation of crystals of the pearlizing agent, and adding an anionic surfactant and a cationic component to the mixture so that at least a portion of the anionic surfactant and at least a portion of the cationic component are each present during crystal formation.

In a third aspect, the present invention is directed to a personal care composition, comprising an aqueous pearlizer concentrate of the present invention.

In fourth aspect, the present invention is directed to a method for modifying the appearance of an aqueous liquid composition, comprising adding to such composition an aqueous pearlizing concentrate of the present invention.

DETAILED DESCRIPTION OF THE INVENTION

In one embodiment, the pearlizing concentrate comprises, based on 100 parts by weight (pbw) of pearlizing concentrate, from about 10 to about 50 pbw, more typically from about 15 to about 40 pbw, and even more typically from about 20 to about 25 pbw, of the pearlizing agent, from about 1 to about 35 pbw, more typically from about 4 to about 30 pbw, and even more typically from about 6 to about 25 pbw, of the anionic surfactant, from about 0.1 to about 20 pbw, more typically from about 0.5 to about 10 pbw, and even more typically from about 1 to about 5 pbw, of the cationic component.

Pearlizing agents are generally known. Pearlizing agents suitable as the pearlizing agent component of the composition of the present invention are those that can be crystallized from a heated mixture of an aqueous medium and molten pearlizing agent by cooling the mixture and that are acceptable for use in the intended end use application. Examples of suitable pearlizing agents include, generally, (C12-C24)alkyl fatty acids, more typically (C14-C22)alkyl fatty acids, oxyalkylene esters of (C12-C24)alkyl fatty acids, more typically oxyalkylene esters of (C14-C22)alkyl fatty acids, such as mono or di esters of alkyl fatty acids with polyethylene glycol, ethylene glycol; or glycerin, (C12-C24)alkanol amides, more typically (C14-C22)alkanol amides, and esters of (C12-C24) alkyl fatty acids, more typically (C14-C22)alkyl fatty acids, with such alkanol amides, as well as mixtures of such pearlizing agents. Specific examples of suitable pearlizing agents include ethylene glycol monolaurate, ethylene glycol monostearate, ethylene glycol monobehenate, ethylene glycol dilaurate, ethylene glycol distearate, ethylene glycol dibehenate, polyethylene glycol monolaurates, polyethylene glycol monostearates, polyethylene glycol monobehenates, polyethylene glycol dilaurates, polyethylene glycol distearates, polyethylene glycol dibehenates, lauric monoethanolamide, stearic monoethanolamide, behenic monoethanolamide, glyceryl stearate, glyceryl behenate, and glyceryl dipalmidate, as well as mixtures thereof. In one embodiment, the pearlizing agent comprises at least one of polyethylene glycol monostearates, polyethylene glycol distearates, ethylene glycol monostearate, and ethylene glycol distearate. More typically, the pearlizing agent comprises at least one of ethylene glycol monostearate and ethylene glycol distearate.

Surfactant compounds are generally known and are characterized by the presence of both a hydrophilic group and a hydrophobic group on the same molecule.

Anionic surfactants are ionic surfactant compounds that have a negative electrical charge associated with the hydrophilic portion of the surfactant. Any anionic surfactant that is acceptable for use in the intended end use application is suitable as the anionic surfactant component of the composition of the present invention. Examples of suitable anionic surfactants include, generally, alkyl sulfonates, aryl sulfonates, alkaryl sulfonates, alpha olefin sulfonates, paraffin sulfonates, alkyl ester sulfonates, alkyl sulfates, alkyl alkoxy sulfates, alkyl alkoxy carboxylates, alkyl alkoxylated sulfates, acylsarcosinates, and amidosulfonates, as well as mixtures thereof. Anionic surfactants are typically associated with a counterion, such as, for example, a sodium, magnesium, potassium, ammonium, or substituted ammonium cation. Specific examples of suitable anionic surfactants include sodium tridecyl benzene sulfonate, sodium trideceth sulfate, sodium dodecyl benzene sulfonate, ammonium lauryl sulfate, ammonium laureth sulfate, triethylamine lauryl sulfate, triethylamine laureth sulfate, magnesium laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, ammonium cocyl sulfate, ammonium lauroyl sulfate, sodium cocyl sulfate, sodium lauroyl sulfate, potassium cocyl sulfate, potassium lauryl sulfate, monoethanolamine cocyl sulfate, sodium lauryl sarcosinate, sodium lauroyl sarcosinate, lauryl sarcosine, and cocyl sarcosine, as well as mixtures thereof.

The cationic component of the composition of the present invention comprises one or more cationic surfactants, cationic polymers, or a mixture thereof.

Cationic surfactants are ionic surfactant compounds that have a positive electrical charge associated with the hydrophilic portion of the surfactant. Any cationic surfactant that is acceptable for use in the intended end use application is suitable as cationic surfactant component of the composition of the present invention Examples of suitable cationic surfactants are include compounds according to formula (1) below:

(1)

wherein:

$R_1$, $R_2$, $R_3$ and $R_4$, are each independently hydrogen, an organic group, provided that at least one of $R_1$, $R_2$, $R_3$ and $R_4$ is not hydrogen.

$X^-$ is an anion.

Suitable anions include, for example, chloride, bromide, methosulfate, ethosulfate, lactate, saccharinate, acetate or phosphate.

If one to three of the $R_1$, $R_2$, $R_3$ and $R_4$ groups are hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine as well as mixtures thereof.

For quaternary ammonium compounds (generally referred to as "quats") $R_1$, $R_2$, $R_3$, and $R_4$ may each independently be the same or different organic group, or alternatively, may be fused with another one of the $R_1$, $R_2$, $R_3$ and $R_4$ groups to form, together with the nitrogen atom to which they are attached, a heterocyclic ring, but may not be hydrogen. Suitable organic groups include, for example, alkyl, alkoxy, hydroxyalkyl, and aryl, each of which may be further substituted with other organic groups. Suitable quaternary ammonium compounds include monoalkyl amine derivatives, dialkyl amine derivatives, and imidazoline derivatives, as well as mixtures thereof.

Suitable monoalkyl amine derivatives include, for example, cetyl trimethyl ammonium bromide (also known as cetrimonium bromide or CETAB), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl-dimethyl-(2)hydroxyethyl ammonium dihydrogen phosphate (also known as hydroxyethyl cetyldimonium phosphate), bassuamidopropylkonium chloride, cocotrimonium chloride, distearyldimonium chloride, wheat germamidopropalkonium chloride, stearyl octyldimonium methosulfate, isostearaminopropal-konium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride, and behenamidopropyl ethyl dimonium ethosulfate, as well as mixtures thereof.

Suitable dialkyl amine derivatives include, for example, distearyldimonium chloride, dicetyl dimonium chloride, stearyl octyidimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bis-stearyldimonium chloride, and mixtures thereof.

Suitable imidazoline derivatives include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Polymers that are suitable as the cationic component are those having at least one cationic site per molecule, and include, for example, guar hydroxypropyltrimonium chloride, hydroxypropyl guar hydroxypropyltrimonium chloride, polymethacrylamidopropyltrimonium chloride, Polyquaternium-2, Polyquaternium-6, Polyquaternium-7, Polyquaternium-10, and Polyquaternium-11, as well as mixtures thereof.

In one embodiment the cationic component comprises at least one of cetrimonium bromide and guar hydroxypropyltrimonium chloride.

The pearlizing concentrate may, optionally, further comprise other ingredients such as, for example, one or more of amphoteric surfactants, Zwitterionic surfactants, nonionic surfactants preservatives, pH adjusting agents, perfumes, dyes, and sequestering agents.

Amphoteric surfactants are ionic surfactant compounds that are characterized by the presence of two ionic sites on the same molecule and which, depending on the pH of the surrounding medium, may carry a negative electrical charge, a positive electrical charge, or both a negative electrical charge and a positive electrical charge on the same molecule. Any amphoteric surfactant that is acceptable for use in the intended end use application is suitable as the optional amphoteric surfactant component of the composition of the present invention. Examples of suitable amphoteric surfactants include derivatives of aliphatic secondary and tertiary amines in which the aliphatic radical may be straight chain or branched, may be saturated or unsaturated, and wherein one of the aliphatic substituents contains from about 8 to about 22 carbon atoms and one contains an anionic water solubilizing group. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates, as well as alkyl iminopropionates, alkyl iminodipropionates and alkyl amphopropylsulfonates. Amphoteric surfactants are typically associated with a counterion, such as, for example, a sodium, magnesium, potassium, ammonium, or substituted ammonium cation. Specific examples of some suitable amphoteric surfactants include sodium cocoamphoacetate, sodium cocoamphopropionate, disodium cocoamphodiacetate, diammonium cocoaphodiacetate, sodium lauroamphoacetate, disodium lauroamphodiacetate, dipotassium lauroamphodiacetate, dimagnesium lauroamphodiacetate, disodium lauroamphodipropionate, disodium cocoamphopropyl sulfonate caproamphodiacetate, sodium caproamphoacetate, disodium caproamphodipropionate, and sodium stearoamphoacetate, and triethanolamine stearoamphoacetate, as well as mixtures thereof.

Zwitterionic surfactants are ionic surfactant compounds characterized by the presence of two ionic sites per molecule, wherein one of the ionic sites carries a positive electrical charge regardless of the pH of the surrounding medium and wherein the other ionic site may, depending on the pH of the surrounding medium, carry a positive charge. Any Zwitterionic surfactant that is acceptable for use in the intended end use application is suitable as the optional Zwitterionic surfactant component of the composition of the present invention. Examples of suitable Zwitterionic surfactants include those which can be broadly described as derivatives of aliphatic quaternary ammonium, phosphonium, and sulfonium compounds in which the aliphatic radicals may be straight chain or branched, may saturated or unsaturated, and wherein one of the aliphatic substituents contains from about 8 to 22 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, sodium cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines, as well as mixtures thereof.

The pearlizing concentrate of the present invention may optionally comprise, based on 100 pbw of the concentrate, a total amount of up to about 35 pbw, more typically from about 0.1 pbw to 20 pbw, even more typically from about 1 pbw to 10 pbw of one or more of Zwitterionic surfactants and amphoteric surfactants.

Nonionic surfactants are surfactant compounds that do not dissociate into ions and that do not have an electrical charge associated with them. Any nonionic surfactant that is acceptable for use in the intended end use application is suitable as the optional nonionic surfactant component of the composition of the present invention. Examples of suitable nonionic surfactants include compounds produced by the condensation of alkylene oxide groups (hydrophilic in nature) with an organic hydrophobic compound which may be aliphatic or alkyl aromatic in nature. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, alkanolamides surfactants, alkylpolyglycosides, and condensation products of aliphatic alcohols with from about 1 to about 25 moles of ethylene oxide. Specific examples of suitable nonionic surfactants include alkanolamides such as cocamide DEA, cocamide MEA, cocamide MIPA, PEG-5 cocamide MEA, lauramide DEA, and lauramide MEA; alkyl-amine oxides such as lauramine oxide, cocamine oxide, cocamidopropylamine oxide, and lauramidopropylamine oxide; polysorbates and ethoxylated sorbitan esters such as sorbitan laurate, sorbitan distearate, PEG-80 sorbitan laurate, polysorbate-20, and polysorbate-80; fatty acids or fatty acid esters such as lauric acid, isostearic acid, and PEG-150 distearate; fatty alcohols or ethoxylated fatty alcohols such as lauryl alcohol, laureth-4, laureth-7, laureth-9, laureth-40, trideceth alcohol, C11-15 pareth-9, C12-13 Pareth-3, and C14-15 Pareth-11, as well as mixtures thereof.

The pearlizing concentrate of the present invention may optionally comprise, based on 100 pbw of the concentrate, a total amount of up to about 20 pbw, typically from about 0.1 pbw to about 15 pbw, and even more typically from about 0.5 pbw to about 10 pbw, of one or more nonionic surfactants (in addition to the pearlizing agent or agents).

In one embodiment, the pearlizing concentrate comprises, based on 100 pbw of the pearlizing concentrate, a total amount of all surfactants, including anionic surfactants and cationic surfactants, as well as any optional Zwitterionic surfactants, amphoteric surfactants, and nonionic surfactants (but excluding the pearlizing agent or agents), of from about 10 to about 35 pbw, more typically, about 15 to about 30 pbw and even more typically from about 18 to about 25 pbw.

Optional components can be utilized in the concentrates of the present invention as a convenient means of incorporation into personal care compositions. Such conventional optional ingredients are well known to those skilled in the art, e.g., preservatives such as benzyl alcohol, methyl paraben, propyl paraben and imidazolidinyl urea; thickeners and viscosity modifiers such as block polymers of ethylene oxide and propylene oxide, e.g. ANTAROX F-88 (Rhodia, Inc.), polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents may each independently be present at levels of up to about 5 pbw, more typically from about 0.01 pbw to about 2.0 pbw, per 100 pbw of the pearlizing concentrate.

Other additional optional additives include electrolytes. Suitable electrolytes generally include, for example compounds having an anion comprising phosphate, chloride, sulfate or citrate and a cation comprising sodium, ammonium, potassium, magnesium, as well as mixtures thereof. Specific examples of suitable electrolytes include sodium chloride, ammonium chloride, sodium sulfate, and ammonium sulfate, as well as mixtures thereof. The pearlizing concentrate of the present invention may optionally comprise, based on 100 pbw of the concentrate, a total amount of up to about 10 pbw, more typically from about 0.5 pbw to 5 pbw, of one or more electrolytes.

The heated aqueous mixture comprising molten pearlizing agent maybe formed in any convenient way, such as for example, adding molten pearlizing agent to a heated aqueous medium, or adding solid pearlizing agent to an aqueous medium, wherein the aqueous medium is initially at ambient temperature, and then heating the resulting mixture to a temperature effective to melt the pearlizing agent, or adding solid pearlizing agent to heated aqueous medium, and then heating the resulting mixture to or maintaining the mixture at a temperature effective to melt the pearlizing agent In general, the aqueous mixture is heated to a temperature at or above the melting point of the pearlizing agent. In those embodiments of the composition of the present invention wherein one or more of the components other than the pearlizing agent are solid materials that are to be incorporated into the composition by melting, the aqueous mixture is typically heated to a temperature that is at or above the melting point of the highest melting of all, that is, including the pearlizing agent, such components. In a typical embodiment, the heated aqueous mixture comprising the pearlizing agent is heated to a temperature of from about 65° C. to about 90° C., more typically from about 70° C. to about 85° C.

In one embodiment, the heated aqueous mixture comprising molten pearlizing agent is stirred to obtain and maintain a two phase mixture wherein a discontinuous phase of molten pearlizing agent is dispersed in continuous phase of aqueous medium. Alternatively, the heated aqueous mixture may be left unstirred after the initial mixing.

The cooling step is conducted at a rate effective to allow formation of crystals of the pearlizing agent. The mixture may simply be allowed to cool to room temperature without taking any action other than discontinuing the heating. More typically, the mixture is cooled by application of a cooling source such as a cooling jacket or cooling coils. In one embodiment, the mixture is stirred during the cooling step to maintain a two phase mixture wherein a discontinuous phase of pearlizing agent is dispersed in a continuous phase of aqueous medium. Alternatively, the heated aqueous mixture may be allowed to cool without stirring. The cooling step can be viewed as comprising three phases, that is, a first phase wherein the temperature of the mixture decreases prior to crystal formation, a second phase wherein crystal formation and growth takes place, and a third phase wherein the temperature of the mixture decreases subsequent to the completion of crystal formation and growth.

In one embodiment, the pearlizing agent is added to an aqueous medium and the resultant mixture is heated at a temperature effective to melt the pearlizing agent and allow formation of a mixture of the molten pearlizing agent and aqueous medium. The pearlizing agent and the aqueous medium may, optionally, each independently be heated prior to addition of the pearlizing agent to the aqueous medium. The anionic surfactant and cationic component may each independently be added to the aqueous medium prior to the heating step, during the heating step, between the heating and cooling steps, or during the cooling step. The entire amount of anionic surfactant or cationic component may each independently be added at any one of such times or, alternatively, multiple additions of portions of the anionic surfactant and cationic component may each independently be made to the mixture at different times.

In one embodiment, at least a portion of the anionic surfactant and at least a portion of the cationic component are each present during crystal formation, that is, at least a portion of the anionic surfactant and at least a portion of cationic component are each independently added to the mixture at any time prior to the formation of crystals in the mixture.

In one embodiment, a mixture of the pearlizing agent and an aqueous medium comprising at least a portion of the anionic surfactant and at least a portion of the cationic component is heated to a temperature effective to melt the pearlizing agent and allow formation of an aqueous mixture comprising molten pearlizing agent and the mixture is then cooled to allow the formation of crystals of the pearlizing agent.

In another embodiment, an aqueous medium comprising at least a portion of the anionic surfactant is heated to a temperature effective to melt the pearlizing agent. The pearlizing agent is then added to the heated aqueous medium and mixed with continued heating to allow formation of a mixture of molten pearlizing agent and aqueous medium. The cationic component is added to the aqueous medium at a time subsequent to the beginning of the heating step. In one embodiment, at least a portion of the cationic component is added during the heating step. In another embodiment, at least a portion of the cationic component is added subsequent to the heating step and prior to the third phase of the cooling step, that is, prior to completion of crystal formation and growth. In one embodiment, at least a portion of the cationic component is added during the first phase of the cooling step, that is, prior to formation of crystals. In another embodiment, at least a portion of the cationic component is added during the second phase of the cooling step, that is, during crystal formation and growth.

In one embodiment, the aqueous pearlescent composition made by the method of the present invention is a pearlescent concentrate of the present invention, as described above. Alternatively, the aqueous pearlescent composition made by the method of the present invention is an end use composition, such as for example, a personal care composition, as further described below.

The pearlizing concentrate of the present invention can be added as a component of a wide variety of personal care compositions. Such compositions can be formulated by one skilled in the art utilizing conventional methods of production. The pearlizing concentrate of the present invention is a "cold" pearlizing concentrate, that is, the concentrate can be added at room temperature. The pearlizing concentrate imparts a specific appearance, in some cases a high luster pearlescence and sheen to the compositions. Generally, the personal care compositions of the present invention can be made by merely mixing, at room temperature, the concentrate of the present invention together with the other components of such composition.

The pearlizing concentrate of the present invention is a "cold" pearlizing concentrate, that is, the concentrate can be blended with another aqueous composition at room temperature. Alternatively, the method of the present invention may be applied to an end use composition, such as for example, a shampoo composition, to form crystals of the pearlizing agent in situ.

Typical personal care products include shampoos, conditioners, hand soap, liquid soap, body wash, facial cleansers, baby cleansers, children's cleansers, and bubble bath. Such products are typically aqueous systems that contain amphoteric surfactants, Zwitterionic surfactants, nonionic surfactants, anionic surfactants, cationic surfactants or combinations thereof. Amphoteric surfactants, Zwitterionic surfactants, nonionic surfactants, anionic surfactants, and cationic surfactants are known and examples of suitable amphoteric surfactants, Zwitterionic surfactants, nonionic surfactants, anionic surfactants, and cationic surfactants include those described above in reference to the pearlizing concentrate of the present invention. Personal care cleansing products typically contain, based on 100 pbw solids (that is absent water and other solvents) of such composition, up to about 6 pbw amphoteric surfactants, up to about 8 pbw Zwitterionic surfactants, up to about 20 pbw anionic surfactants, wherein the total amount of all surfactants ranges from about 6 pbw to about 25 pbw, more typically from about 10 pbw to about 20 pbw.

The personal care compositions utilizing the pearlizing concentrate of the present invention can optionally contain other ingredients, such as, for example, preservatives such as benzyl alcohol, methyl paraben, propyl paraben and imidazolidinyl urea; thickeners and viscosity modifiers such as block polymers of ethylene oxide and propylene oxide, electrolytes, such as sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; conditioning agents such as organosilicon materials, including, silicone gums, polyorganosiloxane fluids, and silicone resins, i.e., crosslinked polyorganosiloxane systems; active ingredients such as antidandruff agents (zinc pyrithion); vitamins or their derivatives such as Vitamin B, Vitamin E Acetate; and sequestering agents such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

The pearlizing concentrate is also useful in modifying the appearance of other aqueous compositions, such as for example, home or automotive care compositions, such as household cleaning compositions and automobile cleaning compositions. Alternatively, the method of the present invention may be applied to an end use home care or automotive care composition to form crystals of the pearlizing agent in situ.

EXAMPLES

The following materials were each used in a number of the compositions set forth in the Examples:

| | |
|---|---|
| Anionic Surfactant 1 | Sodium laureth sulfate, 26 wt % aqueous solution (RHODAPEX ES-2, Rhodia Inc.) |
| Cationic Component 1 | Cetrimonium bromide (RHODAQUAT M242B/99, Rhodia Inc.) |
| Cationic Component 2 | Guar hydroxypropyltrimonium chloride (Jaguar C-17, Rhodia Inc.) |
| Pearlizing Agent 1 | Ethylene glycol distearate |
| Surfactant Blend 1 | An aqueous blend of anionic and nonionic surfactants (ammonium laureth sulfate at a concentration of about 52 wt % in the blend, and cocamide MEA (MIRACARE LAC116, Rhodia Inc.)) |

Examples 1 to 8 and Comparative Examples C1 and C2

The pearlizing concentrates of Examples 1 to 4 and Comparative Example C1 were made by combining the Anionic Surfactant 1, Cationic Component 1, Pearlizing Agent 1, and water in the relative amounts of set forth in Table 1 below, mixing and heating the resulting mixture to 80° C., and then allowing the mixture to cool to room temperature.

TABLE I

| | C. Ex. C1 (pbw) | Ex. 1 (pbw) | Ex. 2 (pbw) | Ex. 3 (pbw) | Ex. 4 (pbw) |
|---|---|---|---|---|---|
| Anionic Surfactant 1 | 58.6 | 58.0 | 57.5 | 56.9 | 56.3 |
| Cationic Surfactant 1 | — | 1.0 | 2.0 | 2.9 | 3.7 |
| Pearlizing Agent 1 | 15.0 | 14.9 | 14.7 | 14.6 | 14.4 |
| Water | 26.4 | 26.1 | 25.9 | 25.6 | 25.4 |

The compositions Examples 5-8 and Comparative Example C2 were made by diluting the pearlizing concentrate compositions of Examples 1-4 and Comparative Example C1 with water, as set forth below in TABLE II. The dilution was necessary in order to study the appearance of the pearl crystals at a concentration more typical of the use level in a finished formulation, such as a shampoo. The relative opacity and shine exhibited by each of the compositions of Examples 5 to 8 and Comparative Example C2 was determined by visually comparison of samples of the compositions that were placed side-by-side and swirled in order to observe the pearl appearance without the settling of the pearl crystals. Relative opacity was rated from 1 (highest) to 6 (lowest). Relative shine was rated from 1 (highest) to 5 (lowest). The opacity and shine results are set forth below in

TABLE II

| | C. Ex. C2 (pbw) | Ex 5 (pbw) | Ex. 6 (pbw) | Ex. 7 (pbw) | Ex 8 (pbw) |
|---|---|---|---|---|---|
| Water | 96 | 96 | 96 | 96 | 96 |
| Pearlizing Concentrate of: | | | | | |
| C. Ex. C1 | 4 | — | — | — | — |
| Ex. 1 | — | 4 | — | — | — |
| Ex. 2 | — | — | 4 | — | — |
| Ex. 3 | — | — | — | 4 | — |
| Ex. 4 | — | — | — | — | 4 |
| Appearance: | | | | | |
| Opacity | 6 | 5 | 3 | 2 | 1 |
| Shine | 5 | 2 | 3 | 4 | 5 |

The results set forth above in TABLE II show that increasing the level of the cationic component increased the opacity of the diluted pearlizing blend and, in some cases, that is, in Examples 5, 6, and 7, the shine of the concentrate is increased as well as the opacity.

Examples 5-8 and Comparative Examples C3 and C4

The pearlizing concentrate compositions of Examples 5-6 and Comparative Example C3 were made by combining the components in the relative amounts indicated below in TABLE III in the following manner. Water and Surfactant Blend 1 were combined and the resulting mixture was then heated to approximately 80° C. Once that temperature was reached, the Pearlizing Agent 1, and either Cationic Component 1 or Cationic Component 2 were then added. Stirring and heating to maintain the 80° C. temperature were each continued (typically about 1 hour or more) until all components of the mixture, including the pearlizer crystals, had dispersed. The heating was then discontinued and the mixture was allowed to cool to room temperature. Comparative Example C3 was made in an analogous manner, but without the addition of the cationic component.

TABLE III

| | C. Ex. C3 (pbw) | Ex. 5 (pbw) | Ex. 6 (pbw) |
|---|---|---|---|
| Surfactant Blend 1 | 30.6 | 30.0 | 30.4 |
| Cationic Component 1 | — | 2 | — |
| Cationic Component 2 | — | — | 0.5 |
| Pearlizing Agent 1 | 20.2 | 19.8 | 20.1 |
| Water | 49.2 | 48.2 | 49.0 |

The shampoo compositions of Examples 7 and 8 and Comparative Example C4 were made by mixing the relative amounts of Surfactant Blend 1 and an electrolyte (sodium chloride), and the pearlizer concentrate of Example 5 or 6 or Comparative Example C3.

The opacity and shine exhibited by each of Examples 7 and 8 and Comparative Example C4 were visually compared after pipetting 2 ml aliquots of the compositions onto a dark surface next to each other. The opacity was rated on a scale of 5 (highest) to 1 (lowest) based on observation of how much of the dark surface beneath the formulations was visible. The shine rated on a scale of 5 (highest) to 1 (lowest) based on observation of how much "glow" was radiating from underneath the surface of the formulations. The opacity and shine results are set forth below in

TABLE IV

| | C. Ex. C4 (pbw) | Ex. 7 (pbw) | Ex. 8 (pbw) |
|---|---|---|---|
| Surfactant Blend 1 | 20 | 20 | 20 |
| Electrolyte | 1.2 | 1.2 | 1.2 |
| Water | 75 | 75 | 75 |
| Pearlizing Concentrate of: | | | |
| C. Ex. C3 | 4 | — | — |
| Ex. 5 | — | 4 | — |
| Ex. 6 | — | — | 4 |
| Appearance: | | | |
| Opacity | 4 | 5 | 5 |
| Shine | 4 | 5 | 5 |

The results set forth above in TABLE IV demonstrate increased opacity and increased shine with the addition of a cationic component when compared in an exemplary cleansing formulation, compared to the same pearlizing concentrate without the inclusion of a cationic component Examples 9-14

The pearlizer concentrate compositions of Examples 9 to 11 were made by combining water, Surfactant Blend 1, Pearlizing Agent 1, Cationic Component 1, and an electrolyte (ammonium chloride) in the relative amounts of set forth below in TABLE V. The compositions were made according to the procedure used in Examples 5 and 6 above, except that the cationic component of compositions of Examples 9 and 10 was not added with the pearlizing agent, but was instead added during cooling of the mixture of water anionic surfactants and pearlizing agent when the mixture had reached the temperature indicated below in Table V.

TABLE V

| | Ex. 9 (pbw) | Ex. 10 (pbw) | Ex. 11 (pbw) |
|---|---|---|---|
| Surfactant Blend 1 | 30.0 | 30.0 | 30.0 |
| Electrolyte | 1 | 1 | 1 |
| Cationic Component 1 | 1 | 1 | 1 |
| Pearlizing Agent 1 | 19.8 | 19.8 | 19.8 |
| Water | 48.2 | 48.2 | 48.2 |
| Temperature at which Cationic Component added (° C.) | 40 | 54 | 80 |

The shampoo compositions of Examples 12-14 were made in the manner describe above for Examples 7 and 8 and Comparative Example C4 using the pearlizing concentrates of Examples 9-11 and the opacity and shine of the shampoo compositions were evaluated according to the protocol described above for Examples 7 and 8 and Comparative Example C4. Results are set forth below in TABLE VI.

TABLE VI

| | Ex. 12 (pbw) | Ex. 13 (pbw) | Ex. 14 (pbw) |
|---|---|---|---|
| Surfactant Blend 1 | 20 | 20 | 20 |
| Electrolyte | 1.2 | 1.2 | 1.2 |
| Water | 75 | 75 | 75 |
| Pearlizing Concentrate of: | | | |
| Ex. 9 | 4 | — | — |
| Ex. 10 | — | 4 | — |
| Ex. 11 | — | — | 4 |
| Appearance: | | | |
| Opacity | 2 | 5 | 5 |
| Shine | 3 | 3 | 3.5 |

The results set forth above in TABLE VI show the effect on the pearlizing concentrate when the cationic component is incorporated at different temperatures during the cooling step. The shampoo composition of Example 12 contained the pearlizing concentrate of Example 9, wherein the cationic component was added to the pearlizing concentrate at 40° C. (after the crystallization is believed to be primarily completed). The shampoo composition of Example 13, contained the pearlizing concentrate of Example 10, wherein the cationic component was added at 54° C. (believed to be approximately when the crystallization would start to occur). The shampoo composition of Example 14, contained the pearlizing concentrate of Example 11, wherein the cationic component was added at 80° C. along with the pearlizing agent.

Examples 15-18 and Comparative Examples C5 and C6

The pearlizer concentrate compositions of Examples 15 and 16 were made by combining water, Surfactant Blend 1, Pearlizing Agent 1, Cationic Component 1 and an electrolyte (ammonium chloride) in the relative amounts of set forth below in TABLE VII. Comparative Example C5 was made in an analogous manner, but without the addition of the cationic component.

TABLE VII

| | Ex. 15 (pbw) | Ex. 16 (pbw) | C. Ex. C5 (pbw) |
|---|---|---|---|
| Surfactant Blend 1 | 30.0 | 29.7 | 30.3 |
| Electrolyte | 1 | 1 | 1 |
| Cationic Component 1 | 1 | 2 | — |
| Pearlizing Agent 1 | 19.8 | 19.6 | 20.0 |
| Water | 48.2 | 47.7 | 48.7 |
| Temperature at which Cationic Component added (° C.) | 80 | 80 | N/A |

The shampoo compositions of Examples 17 and 18 and of Comparative Example C6 were made in the manner described above for Examples 7 and 8 and Comparative Example C4, using the pearlizing concentrates of Examples 15 and 16 and of Comparative Example C5 and the opacity and shine of the shampoo compositions were evaluated according to the protocol described above for Examples 7 and 8 and Comparative Example C4. Results are set forth below in TABLE VIII.

TABLE VIII

| | C. Ex. C6 (pbw) | Ex. 17 (pbw) | Ex. 18 (pbw) |
|---|---|---|---|
| Surfactant Blend 1 | 20 | 20 | 20 |
| Electrolyte | 1.2 | 1.2 | 1.2 |
| Water | 75 | 75 | 75 |
| Pearlizing Concentrate of: | | | |
| C. Ex. C5 | 4 | — | — |
| Ex. 15 | — | 4 | — |
| Ex. 16 | — | — | 4 |
| Appearance: | | | |
| Opacity | 2.5 | 5 | 4.5 |
| Shine | 4 | 3.5 | 5 |

The results set forth above in TABLE VIII demonstrate additional examples of increased opacity and, in some cases, increased shine with the addition of a cationic component, compared in an exemplary cleansing formulation to the same pearlizing concentrate without the inclusion of a cationic component. The compositions of Examples 17 and 18 each exhibited increased opacity. The composition of Example 18 also exhibited increased shine.

Examples 19-21

The pearlescent liquid hand soap of Example 19 is made by combining 60.6 pbw water, 23.4 pbw of a 40 wt % aqueous solution of sodium a olefin sulfonate (RHODACAL A-246-L, Rhodia, Inc.), 12 pbw of the pearlizing concentrate of Example 2, citric acid, sodium chloride, a perfume, a dye and a preservative. The water is charged into a mixing vessel and the other components are slowly mixed at room temperature until the mixture becomes uniform in appearance and texture. Citric acid (50 wt %) is then added in an amount sufficient to adjust the pH to 6.0. The sodium chloride, perfume, dye and preservative are then added.

The ultra-mild body shampoo of Example 20 is made by combining 62.4 pbw deionized water, 17.2 pbw of a first anionic surfactant (sodium lauryl sulfate, 29.5 wt % active (RHODAPON SB-8208/s, Rhodia, Inc.)), 4.2 pbw of a second anionic surfactant (disodium laureth (3EO) sulfate sulfo succinate, 30 wt % active (GERPOPON SBFA 30, Rhodia, Inc.)), 8.5 pbw of the pearlizing concentrate of Example 6, 7.7 pbw of a Zwitterionic surfactant (cocamido propyl betaine, 30 wt % active MIRATINE BET C-30 (Rhodia, Inc.)), sodium chloride, a perfume, a dye, a preservative. The water is charged into a mixing vessel and the other components are slowly mixed at room temperature until the mixture becomes uniform in appearance and texture. The sodium chloride, perfume, dye and preservative are then added.

The mild conditioning shampoo composition of Example 21 is made by combining 30 pbw of a shampoo blend (sodium methyl cocoyl taurate, cocoamidopropyl betaine, cocoamide DEA and glycerine) 5 pbw of an anionic surfactant (sodium laureth sulfate, 70 wt % active (RHODAPEX 3N70, Rhodia, Inc.)), 3 pbw of an amphoteric surfactant (sodium cocoamphoacetate, 40 wt % active (MIRANOL Ultra C-32, Rhodia, Inc.)), 2 pbw of a nonionic surfactant (cocoamide DEA (ALKAMIDE DC 212/S, Rhodia, Inc.), 6 pbw of a dimethicone emulsion (MIRASIL DM-E, Rhodia, Inc.), 4 pbw of the pearlizing concentrate of Example 5, sodium chloride, a fragrance, a dye, a preservative and water. The water is charged into a mixing vessel and the other components are slowly mixed at room temperature until the mixture becomes uniform in appearance and texture. The sodium chloride, perfume, dye and preservative are then added.

Incorporating an anionic surfactant and a cationic component into the pearlizing concentrate is useful for the preparation of high opacity appearance and in some cases high shine as well. While not wishing to be bound by the theory, it is believed that the presence of the anionic surfactant and cationic component influences the crystallization of the pearlizing agent as the crystals are formed and alters the crystal structure of the pearlizing agent to thereby alter the appearance of the concentrate and personal care product made therefrom.

What is claimed is:

1. A method for making an aqueous pearlescent composition, comprising providing a heated aqueous mixture comprising a molten pearlizing agent, cooling the mixture to allow formation of crystals of the pearlizing agent, and adding an anionic surfactant and a cationic component to the mixture so that at least a portion of the anionic surfactant and at least a portion of the cationic component are each present during crystal formation, wherein the anionic surfactant is added to the aqueous mixture prior to the cooling step and wherein the at least a portion of the cationic components is added to the aqueous mixture during the cooling step.

2. The method of claim 1, wherein the heated aqueous mixture is at a temperature of from about 65° C. to about 90° C.

3. The method of claim 1, wherein at least a portion of the cationic component is added to the aqueous mixture prior to the cooling step.

* * * * *